(12) United States Patent
Little et al.

(10) Patent No.: US 7,331,244 B1
(45) Date of Patent: Feb. 19, 2008

(54) STAMPING PRESS LINE SIMULATION DEVICE AND METHOD

(75) Inventors: Jimmy Little, Galloway, OH (US); Chris Current, Urbana, OH (US)

(73) Assignee: Honda Motor Co., Ltd., Tokyo (JP)

( * ) Notice: Subject to any disclaimer, the term of this patent is extended or adjusted under 35 U.S.C. 154(b) by 120 days.

(21) Appl. No.: 11/278,251

(22) Filed: Mar. 31, 2006

(51) Int. Cl.
*G01N 3/10* (2006.01)

(52) U.S. Cl. .......................................... 73/825; 72/17.3

(58) Field of Classification Search .................. 73/825; 72/17.3
See application file for complete search history.

(56) References Cited

U.S. PATENT DOCUMENTS

| | | | |
|---|---|---|---|
| 2,412,413 | A | 12/1946 | Moss |
| 3,273,384 | A | 9/1966 | Flaugher |
| 4,375,162 | A | 3/1983 | Eppley |
| 4,591,093 | A | 5/1986 | Elliott, Jr. |
| 4,854,165 | A | 8/1989 | Jay |
| 5,213,726 | A | 5/1993 | Ramsey et al. |
| 5,333,488 | A | 8/1994 | Ramsey et al. |
| 5,450,756 | A | 9/1995 | Kirii et al. |
| 5,641,918 | A | 6/1997 | Odenwald |
| 5,682,657 | A * | 11/1997 | Hirose ........................ 29/33 J |
| 6,112,578 | A | 9/2000 | Black et al. |
| 6,220,137 | B1 * | 4/2001 | Matsuoka ..................... 83/627 |
| 6,272,902 | B1 | 8/2001 | Chen et al. |
| 6,769,280 | B2 * | 8/2004 | Cao et al. ..................... 72/17.3 |
| 7,130,708 | B2 * | 10/2006 | Wang et al. ................. 700/111 |
| 2002/0186007 | A1 * | 12/2002 | Cao et al. ............. 324/207.16 |
| 2003/0019267 | A1 * | 1/2003 | Futamura et al. ............ 72/21.3 |
| 2005/0022583 | A1 | 2/2005 | Weigel |
| 2005/0126254 | A1 * | 6/2005 | Fidziukiewicz ............ 72/452.9 |
| 2006/0249038 | A1 * | 11/2006 | Futamura et al. ........... 100/281 |
| 2006/0283229 | A1 * | 12/2006 | Futamura et al. ............. 72/443 |
| 2007/0193331 | A1 * | 8/2007 | Futamura et al. ............. 72/454 |

* cited by examiner

*Primary Examiner*—Edward Lefkowitz
*Assistant Examiner*—Freddie Kirkland, III
(74) *Attorney, Agent, or Firm*—Rankin, Hill, Porter & Clark LLP; Vincent Ciamacco

(57) ABSTRACT

An apparatus and method for testing a stamping press die that has includes a plurality of mechanical devices. The apparatus includes a plurality of pneumatic connections for supplying pressurized air to each of the plurality of mechanical devices; a plurality of valves for regulating pressurized air to associated connections at a predetermined pressure and flow, so as to actuate the associated mechanical devices; and a control system for selectively controlling the plurality of valves, so as to implement a predetermined sequence of valve actuations. In this way, the control system simulates a predetermined sequence of mechanical device operation while the die is removed from the stamping press.

9 Claims, 5 Drawing Sheets

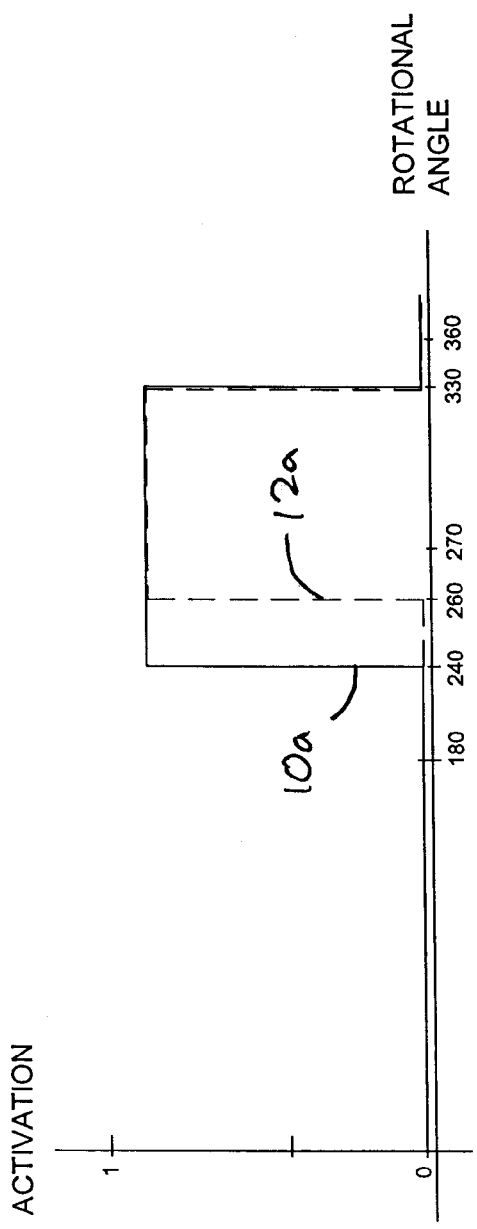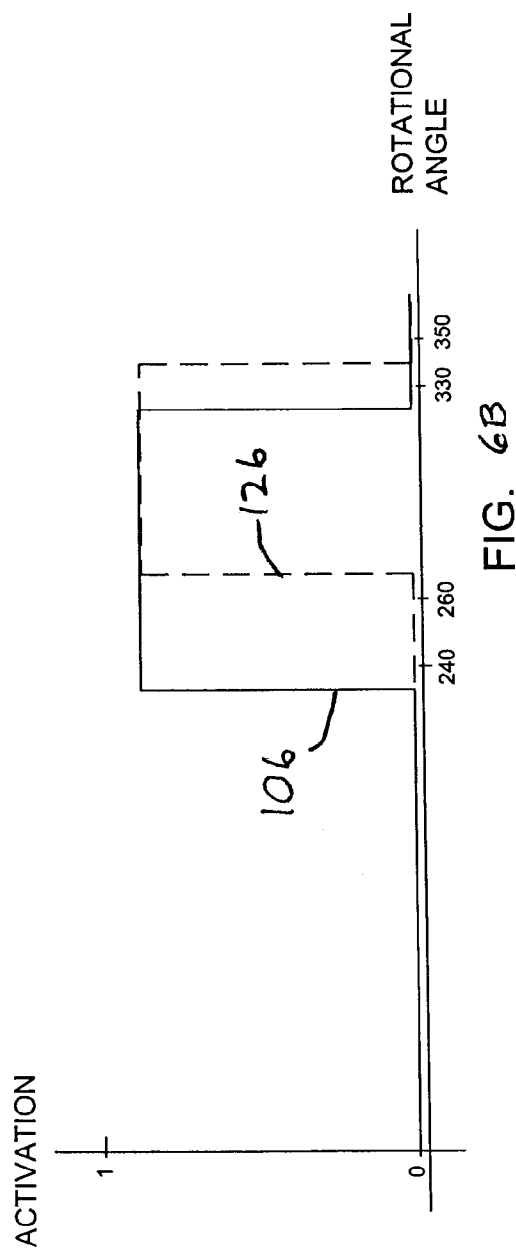

STAMPING PRESS LINE SIMULATION DEVICE AND METHOD

BACKGROUND OF THE INVENTION

1. Field of the Invention

The present invention is directed toward stamping presses and, more particularly, toward a method and apparatus for simulating stamping press operation.

2. Description of the Related Art

A stamping press is used to form parts using a large application of force. Stamping is typically used to form metal parts, such as vehicle body panels, from sheet metal. A stamping die set is held in the stamping press, and typically includes a fixed die and a moving die or punch. The fixed die remains stationary on a bottom section of the stamping press. The punch is maintained above while the press is in an open position. A sheet metal blank is placed on the fixed die. A ram drives the punch against the blank and toward the fixed die, thereby forming the blank into a shape of the die set.

It is advantageous to incorporate one or more secondary mechanical devices into at least one of the dies. These devices are beneficial for part handling and for custom-forming specific features into the stamped product. Four basic types of mechanical devices are used in vehicle body panel die blocks. A drop cam is used to form side panels. A cam slider shifts forward in the lower die to eject a formed part. A scrap kicker cuts the trimmings off the edges of the die and kicks them down a chute to be recycled. And a panel lifter pushes the stamped part to permit the part to be lifted out of the die. It is appreciated that some dies for some operations can include three or fewer mechanical devices, depending on the stamping operation.

The timing of operation of the mechanical devices is crucial. For example, if a mechanical device activates before the punch finishes its stroke, misalignment of the stamped part may result, and therefore cause scrapped parts. Also, such misalignment can result in damage to the mechanical devices and/or the die set. The same sort of damage can result if the punch retracts before the mechanical device completes its stroke.

The actuations of the main punch and any secondary devices can be expressed as a function of "rotational angle". It is to be appreciated that "rotation" corresponds to a single die movement cycle of 360 degrees. The rotational angle of the mechanical devices corresponds to an associated actuation timing within a stamping cycle. FIG. 6A shows rotational angles corresponding to normal operation of a stamping press having a main punch and a secondary mechanical device. As indicated, a punch operation 10a is actuated or advanced at a rotational angle of 240 degrees and retracted at a rotational angle of 330 degrees in a stamping cycle. A mechanical device operation 12a is actuated at 260 degrees in the cycle, after the punch has engaged the material. The mechanical device operation 12a is retracted just before 330 degrees in the cycle, so that the mechanical device will not interfere with retraction of the punch.

However, upon setting up a new die set, or when an existing die set undergoes routine servicing, it is common to experience timing issues with the presses that result in the rotational angles of the various die actuations being out of phase. During servicing, the entire die set may be disassembled, and the pneumatic lines may be disconnected and reconnected. The existing test units for confirming stamp die operation after maintenance include a manually operated hand valve that only allows one mechanical device to be operated at a time. Also, each device must be tested at the repair area pressure and volume, irrespective of its online operation pressure and volume. This introduces errors into the mechanical devices, resulting in changes to their timing, i.e. their effective rotational angles of operation.

As shown in FIG. 6B, the punch operation 10b may be out of phase five degrees ahead of normal (i.e., five degrees leading), actuating at a rotational angle of about 235 degrees and retracting at about 325 degrees. Meanwhile, the mechanical device operation 12b may be out of phase five degrees behind normal (i.e., five degrees lagging), actuating at about 265 degrees and retracting at about 335 degrees. As seen from the figure, the mechanical device would still be extended while the punch is retracting, and may result in the die set hanging up during retraction, which could damage the part and any of the interfering die components.

SUMMARY OF THE INVENTION

The difficulties and drawbacks associated with previous-type systems are overcome by the present apparatus and method for testing a die set for use in a stamping press. The die set includes first and second dies, at least one of which having a plurality of mechanical devices. The apparatus of the present invention includes a plurality of pneumatic connections for supplying pressurized air to each of the plurality of mechanical devices. A plurality of valves is also provided for regulating air flow to each of the plurality of connections, so as to actuate the associated mechanical devices. A control system selectively actuates the plurality of valves, so as to implement a predetermined sequence of valve actuations. In this way, the control system simulates a predetermined sequence of mechanical device operation without operation of the stamping press such that the simulation can be accomplished when the die set is removed from the stamping press.

BRIEF DESCRIPTION OF THE DRAWINGS

These and further features of the invention will be apparent with referenced to the following description and drawings, wherein.

DETAILED DESCRIPTION OF THE PREFERRED EMBODIMENTS

Figure 1:
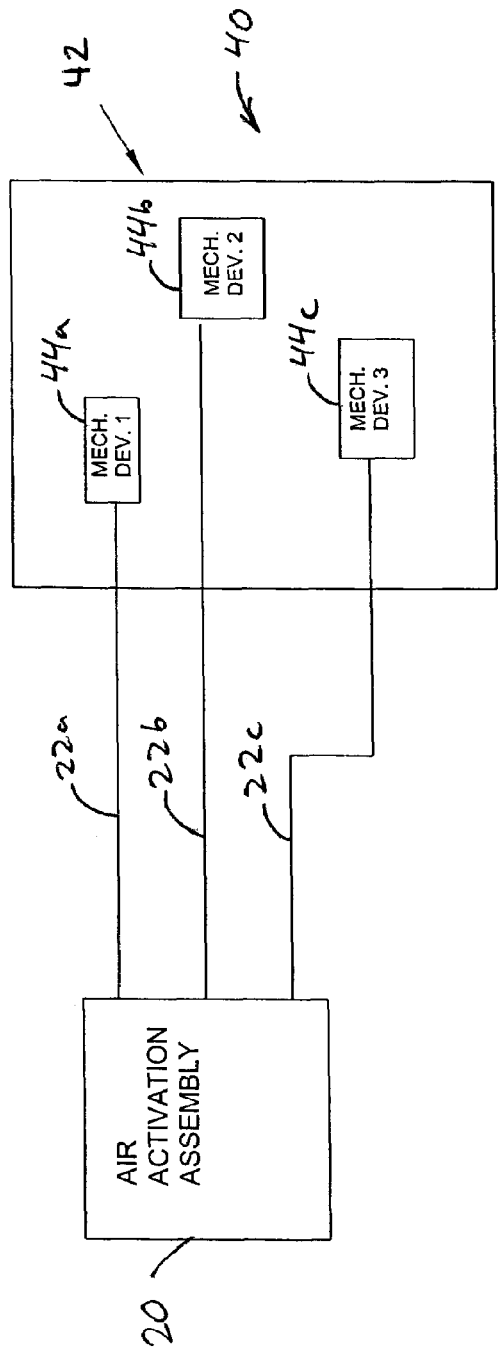
FIG. 1 schematically depicts the air actuation assembly and its interaction with the mechanical devices in a stamping die, in accordance with the present invention.

The present invention is particularly provided to operate a die set for a stamping press in such a way as to mimic production line conditions in connection with the mechanical devices, but without actually operating the press and without requiring the die set to be disposed within the stamping press. The present invention allows the operation of multiple mechanical devices at the same time using the same pneumatic pressure and volume as would be used in an actual manufacturing production line. The timing of the activation and deactivation of the multiple mechanical devices is adjusted to the current speed of the manufacturing production line.

Turning now to the figures, it is understood that like reference numerals refer to like components. It is also understood that a method of testing a stamping die or die set follows from the operation of the herein-disclosed apparatus. Generally speaking, the present invention includes an air actuation assembly or apparatus 20 and a method for testing a stamping die set 40 including first and second dies, at least one of which has a plurality of mechanical devices 44a, 44b, 44c. The apparatus 20 includes a plurality of pneumatic connections 22a, 22b, 22c for supplying pressurized air to each of the mechanical devices 44a, 44b, 44c.

A plurality of valves 24a, 24b, 24c are also provided for controlling air flow to an associated one of the plurality of connections 22a, 22b, 22c at a predetermined pressure and flow, so as to actuate the associated mechanical devices 44a, 44b, 44c. A control system 30 is included for selectively controlling the plurality of valves 24a, 24b, 24c, so as to implement a predetermined sequence of valve actuations. In this way, the control system 30 simulates a predetermined sequence of mechanical device operation. The simulation can take place without operation of the stamping press and with the die set 40 removed from the stamping press. For example, the die set could be disposed in a storage or repair area.

In the preferred embodiment, the air actuation assembly 20 is a portable device that can be moved from place to place within a stamping plant for servicing a number of different stamping die sets 40. It should be appreciated that the air actuation assembly 20 is a self-contained unit. All its presently disclosed components are preferably retained within a housing so that the unit can be moved. It is also contemplated that the unit housing could be mounted on wheels, so as to facilitate movement between different stamping press stations.

FIG. 1 schematically illustrates the air actuation assembly or apparatus 20 for testing one die 42 of a die set 40. The procedure for testing of the other die of the die set 40 will be substantially identical, and will not be repeated hereinafter. Further, although most conventional die sets 40 include a first die and a second die, it is also contemplated that a die set can be used having more than two die components, e.g. four die components. The illustrated die 42 is a stationary die block having the plurality of mechanical devices 44a, 44b, 44c formed therein. The die 42 also includes a reciprocal punch for being lowered into the stationary die block to form a stamped part.

It should be appreciated that the mechanical devices 44a, 44b, 44c can be any common mechanical device used in a die block. For example, the mechanical devices 44a, 44b, 44c can include one or more of a drop cam, a cam slider, a scrap kicker and/or a panel lifter, as described hereinabove. It should be appreciated that the present invention also contemplates using any other suitable type of mechanical device.

Figure 2:
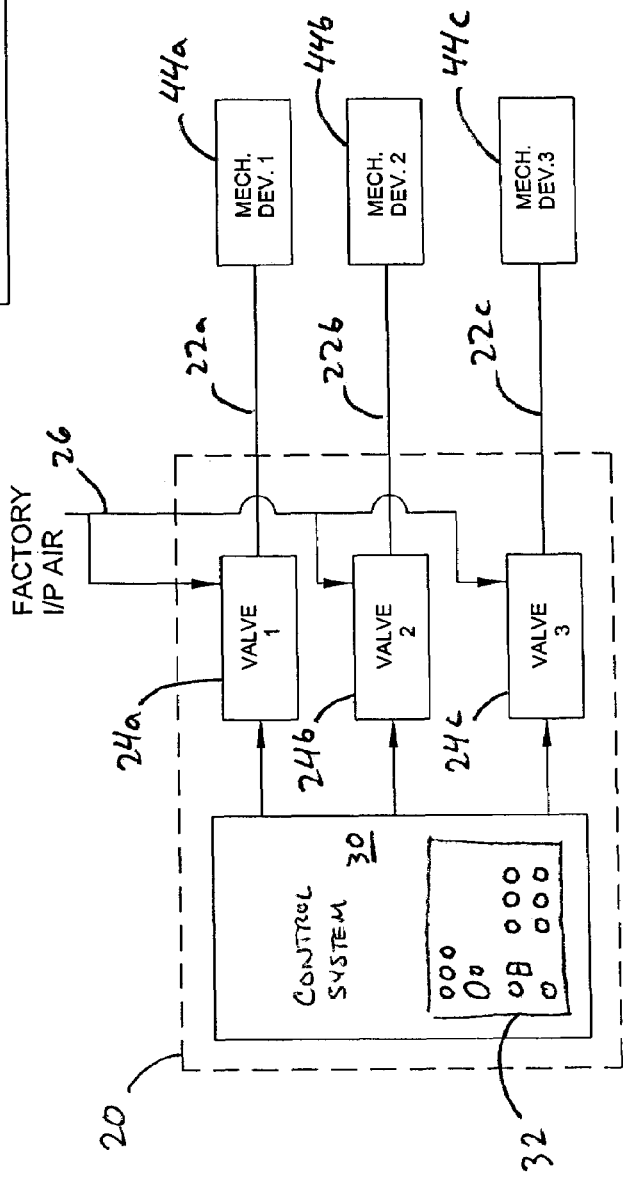
FIG. 2 is a detailed schematic of the device in FIG. 1, showing internal structures of the air actuation assembly, including a control panel and a valve arrangement, in accordance with the present invention.
Figure 3:
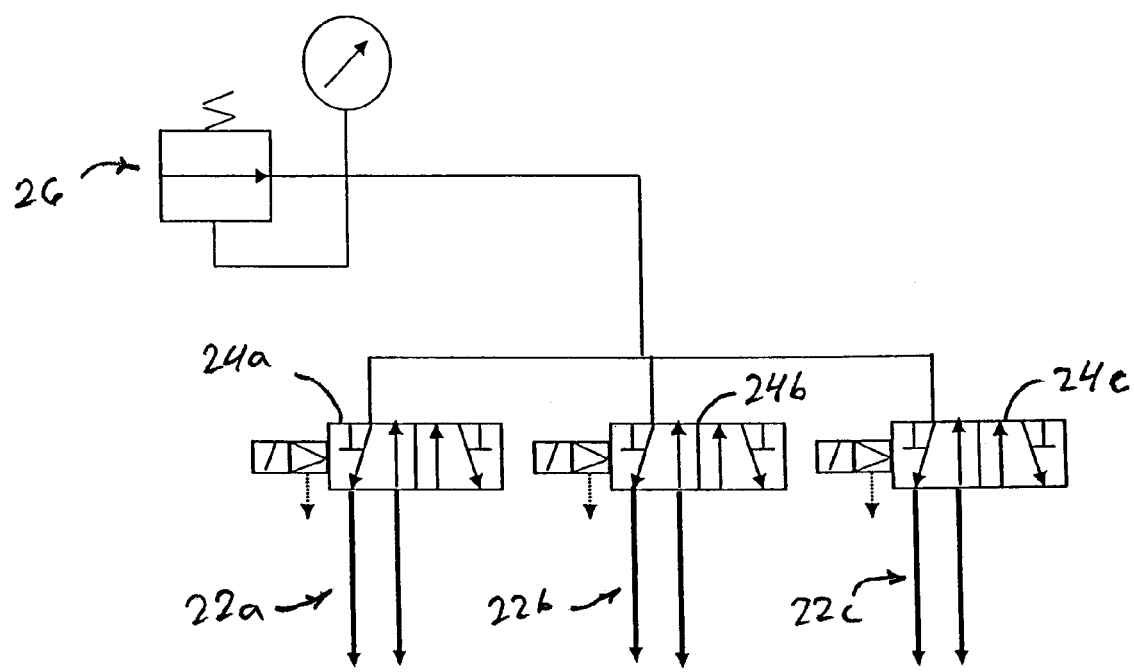
FIG. 3 schematically illustrates a valve arrangement in accordance with the present invention.

As shown in FIGS. 1, 2 and 3, the present air actuation assembly 20 connects with the plurality of pneumatic connections 22a, 22b, 22c that supply pressurized air to an associated one of the mechanical devices 44a, 44b, 44c. As shown in FIG. 3, each of the pneumatic connections 22a, 22b, 22c preferably include a pair of pneumatic hoses. In the preferred embodiment, the mechanical devices 44a, 44b, 44c are preferably double-acting cylinder devices. One of the pair of hoses supplies a positive pressure to actuate the cylinder, while the other hose supplies a negative pressure, to de-actuate the cylinder, as is understood in the art.

The plurality of pneumatic connections 44a, 44b, 44c are preferably color-coded hoses, extending from the apparatus 20 to the associated plurality of mechanical devices. This arrangement permits a quick, flexible connection and easy identification of an air line associated with a particular device. The hoses can be color-coded to indicate the firing order of the mechanical devices in a particular die. For example, a red/yellow hose combination can be used for the first pneumatic connection 44a; black/white for the second pneumatic connection 44b; and blue/green for the third pneumatic connection 44c.

The hose diameters and lengths in the present activation assembly 20 are preferably the same as those used in online conditions, so as to insure that corresponding pressure drops are delivered to the mechanical devices 44a, 44b, 44c. Of course, any suitable pneumatic connection can be employed without departing from the invention.

It should be further appreciated that three pneumatic connections and associated mechanical devices are simply shown for descriptive purposes. Naturally, the present invention is not limited to only three mechanical devices with associated pneumatic supply components.

As shown in FIG. 2, the air actuation assembly 20 incorporates the plurality of valves 24a, 24b, 24c for regulating the pressure and volume of pressurized air flow to an associated one of the plurality of connections 22a, 22b, 22c. As specifically indicated in FIG. 3, the valves 24a, 24b, 24c are preferably electronically-actuated solenoid valves, such as the type sold by Rexroth Mecman AB of Stockholm, Sweden. In this way, the associated mechanical devices 44a, 44b, 44c can be actuated at the pressure and volume that would occur during normal operation on the manufacturing production line. This is an important factor in maintaining the timing of the mechanical devices, i.e. maintaining the proper rotational angles of actuation on the manufacturing production line.

The air actuation assembly 20 includes a connection to a factory input air supply 26. Preferably, the factory air supply 26 is at 80 psi so as to deliver a pressure and volume equal to or greater than that required by the mechanical devices 44a, 44b, 44c. It is understand that the associated plurality of connections 22a, 22b, 22c and valves 24a, 24b, 24c may be sized and configured to step down the pressure and volume as needed in order to supply the desired air pressure and volume for the components. Optionally, the air actuation assembly 20 may also include a portable compressor for generating actuation air within a device housing or cabinet.

The air actuation assembly 20 further includes a control system 30 for selectively controlling the plurality of valves 24a, 24b, 24c. The control system 30 implements a predetermined sequence of valve actuations, so as to simulate a predetermined sequence of mechanical device operations without actually operating the stamping press.

In the preferred embodiment, the control system 30 is a programmable logic controller (PLC) as is typically used in the field of manufacturing process control. Preferably an Automation Direct DL 240 PLC is used. However, it is understood that any suitable electronic control system could also be used, without departing from the invention. The PLC can be activated using a control panel 32 that includes a plurality of hand controls. The controls are preferably mounted on the control panel 32, which is retained on a top surface of the air actuation assembly 20. These controls are thus connected to the PLC input section in a conventional manner, as is understood in the art. The valves 24*a*, 24*b*, 24*c* are connected to the PLC output section in the conventional manner as is also understood in the art.

Figure 4:
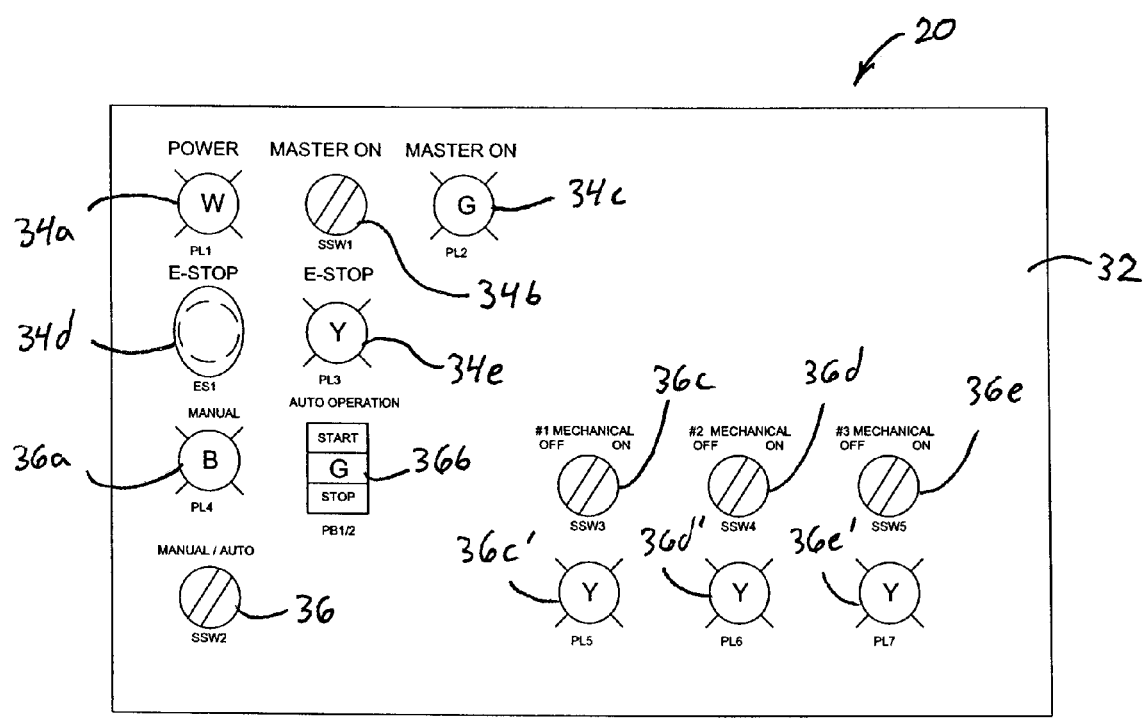
FIG. 4 is a detail view of the control panel generally indicated in FIG. 2, in accordance with the present invention.

As shown in FIG. 4, the controls can be enabled when a white POWER indicator light 34*a* is illuminated. When POWER 34*a* is indicated, the air actuation assembly 20 can be activated by a MASTER ON switch 34*b*, which is selected between an ON and an OFF position. A green MASTER ON indicator light 34*c* indicates that the air actuation assembly 20 is ready to operate. During operation of the mechanical devices 44*a*, 44*b*, 44*c*, it may be necessary to stop operation in the event of an emergency situation. An emergency stop or E-STOP switch 34*d* is provided to stop the air actuation assembly 20. A red indicator light 34*e* illuminates when the E-STOP 34*d* is activated. It should be appreciated that all the indicator lights disclosed herein are also connected to the PLC output section, as is again understood in the art.

A MANUAL/AUTO switch 36 is provided for selecting between a manual operation mode and an automatic operation mode. In the manual operation mode, the PLC enables a user to manually activate each mechanical device 44*a*, 44*b*, 44*c*. In automatic operation mode, the PLC automatically implements the predetermined sequence of valve actuation in accordance with an operational simulation algorithm. When the MANUAUAUTO switch 36 is in manual mode, a blue indicator MANUAL indicator light 36*a* is illuminated. When the MANUAL/AUTO switch 36 is turned to automatic mode, an AUTO OPERATION toggle switch 36*b* is enabled. The AUTO OPERATION toggle 36*b* includes a green indicator light to indicate enablement of automatic mode, and two actuation positions corresponding to START and STOP.

When the manual mode is enabled, the PLC enables a plurality of manual controls 36*c*, 36*d*, 36*e*. Each of the manual controls 36*c*, 36*d*, 36*e* are used for selectively actuating an associated one of the plurality of valves 24*a*, 24*b*, 24*c* in accordance with a manually-operated sequence. As indicated in FIG. 3, the manual controls 36*c*, 36*d*, 36*e* are switches selectable between ON and OFF states. When each of the manual controls 36*c*, 36*d*, 36*e* are ON, an associated yellow indicator light 36*c'*, 36*d'*, 36*e'* is illuminated.

In operation of the present air actuation assembly 20, the manual switches 36*c*, 36*d*, 36*e* can be actuated in order to manually sequence through each mechanical device 44*a*, 44*b*, 44*c* or in any desired manner in order to test performance of the associated die 42. In automatic mode, the PLC will automatically sequence through each mechanical device 44*a*, 44*b*, 44*c* at a rate comparable to line operation. Optionally, this rate can be adjusted as needed by reprogramming the PLC, in order to match a specific line speed.

In the preferred embodiment, in the automatic mode, the present control system 30 implements the predetermined sequence of valve actuations in accordance with predetermined rotational angles associated with each of the plurality of mechanical devices 44*a*, 44*b*, 44*c*. These rotational angles are synchronized so that the timing of the mechanical devices 44*a*, 44*b*, 44*c* can be measured against that of the stamping press 40 in operation.

In one aspect of the invention, the air actuation assembly 20 can be used to configure a newly-installed die set 40 or to reconfigure repaired mechanical devices after servicing.

The air actuation assembly 20 allows sticking points for malfunctioning parts to be quickly identified and adjusted. In another aspect of the invention, the present air actuation assembly 20 can be used as a troubleshooting tool. In this way, a single die technician can allow the system to cycle in automatic mode and observe the die 42 for any operational problems. This is an improvement over a previous-type troubleshooting procedure in which two technicians were required, one to operate a hand valve, and another to monitor device operation.

Figure 5:
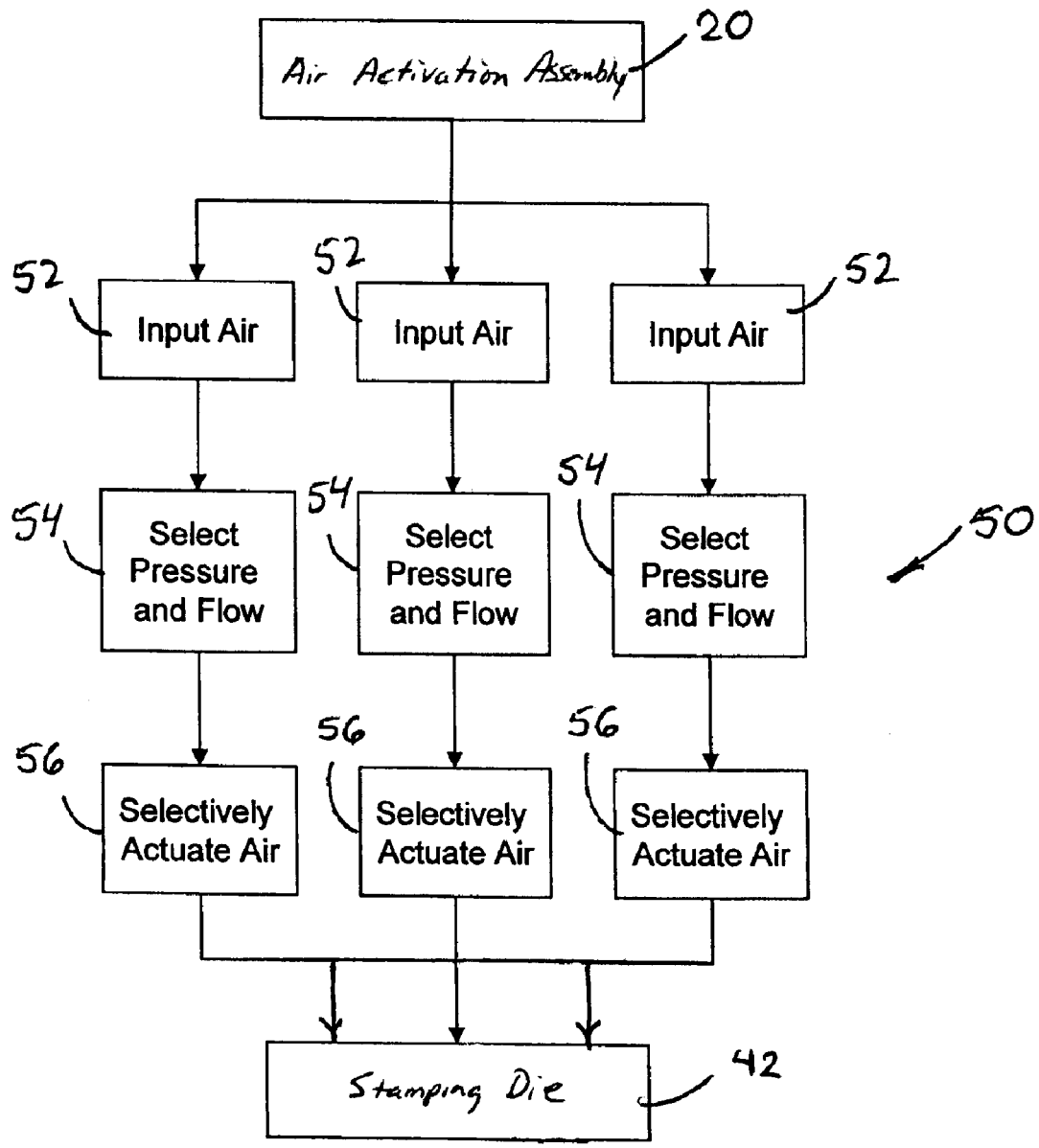
FIG. 5 is a flow chart showing the operational steps in a method implemented by the apparatus in accordance with the present invention; and, FIGS. 6A and 6B respectively show the rotational angles of the die and a single mechanical device of a properly-operating conventional-type stamping press and an improperly operating stamping press.

A method 50 of testing a die 42 in accordance with the present air actuation assembly 20 is generally indicated in FIG. 5. The die 42 to be tested includes a plurality of mechanical devices 44*a*, 44*b*, 44*c*.

The testing method includes a step 52 of supplying input air through a plurality of pneumatic connections 22*a*, 22*b*, 22*c*, where each of the plurality of pneumatic connections 22*a*, 22*b*, 22*c* are associated with one of the plurality of mechanical devices 44*a*, 44*b*, 44*c*. A step 54 follows of selecting a predetermined pressure and flow of the input air to each of the plurality of connections 22*a*, 22*b*, 22*c*, so as to actuate the associated mechanical devices 44*a*, 44*b*, 44*c*. A step 56 follows of selectively actuating the input air to each of the plurality of pneumatic connections 22*a*, 22*b* 22*c*, so as to implement a predetermined actuation sequence, so as to simulate a predetermined sequence of mechanical device operation. It is understood that the step 56 of selectively actuating the input air is performed with the associated plurality of valves 24*a*, 24*b*, 24*c*, as had been disclosed hereinabove.

The step 56 of selectively actuating comprises selectively actuating the predetermined actuation sequence in accordance with a manually-operated sequence. In reference to the control panel 32 disclosed above, the step 56 can be implemented by first insuring that the electrical and pneumatic connections are all in place, that the MASTER ON switch 34*b* is activated, and that the MANUAL/AUTO switch 36 is turned to the manual mode position. Each manual control switch 36*c*, 36*d*, 36*e* is moved to the ON position to activate the desired mechanical device 44*a*, 44*b*, 44*c*. When finished, each switch 36*c*, 36*d*, 36*e* is moved back to the OFF position. The E-STOP switch 34*d* is used in the event a mechanical device 44*a*, 44*b*, 44*c* must be quickly deactivated. When the manual test is finished, the MASTER ON switch is turned off.

Alternatively, this step 56 of selectively actuating can be performed by automatically implementing the predetermined actuation sequence in accordance with an operational simulation algorithm. With the MANUAL/AUTO switch 36 turned to automatic mode, the mechanical devices 44*a*, 44*b*, 44*c* to be tested are selected by turning ON the corresponding switches 36*c*, 36*d*, 36*e*. Pressing START on the AUTO OPERATION button 36*b* will begin the automatic actuation sequence algorithm. The devices 44*a*, 44*b*, 44*c* will be activated one at a time in accordance with the algorithm. The device timings correspond to the device rotational angles in an actual stamping operation. At the end of a cycle, the device actuation will stop and then begin another cycle until STOP is pushed on the AUTO OPERATION button 36*b*, or until the E-STOP button 34*d* is pressed. When finished, the switches 36*c*, 36*d*, 36*e* are turned off, and the MANUAL/AUTO switch 36 is turned to manual mode, after which the MASTER ON is turned off.

The present method also includes an initial setup routine. The initial setup routine includes a step of measuring air pressure and volume to each of the plurality of mechanical devices 44*a*, 44*b*, 44*c* using an air flow gauge and also a pressure gauge. Measurements are preferably taken where the hoses connect to the associated plurality of mechanical devices 44a, 44b, 44c. The measurements are preferably taken from idle mechanical device hoses during an actual run in order to closely approximate running conditions. These measurements are compared with predetermined values recorded on a control document.

As described hereinabove, the present invention therefore solves many problems associated with previous type methods and implementations. However, it will be appreciated that various changes in the details, materials and arrangements of parts which have been herein described and illustrated in order to explain the nature of the invention may be made by those skilled in the art within the principle and scope of the invention will be expressed in the appended claims.

What is claimed is:

1. An apparatus for testing a stamping press die, said die having a plurality of mechanical devices, said apparatus comprising:
   a plurality of pneumatic connections for supplying pressurized air to each of the plurality of mechanical devices;
   a plurality of valves for regulating pressurized air to an associated one of the plurality of connections at a predetermined pressure and flow, so as to actuate the associated mechanical devices; and
   a control system for selectively controlling the plurality of valves so as to implement a predetermined sequence of valve actuations and thereby simulate a predetermined sequence of mechanical device operation,
   wherein the apparatus is a self-contained portable device that can be transported from place to place to test a number of different die sets.

2. The apparatus of claim 1, wherein the plurality of pneumatic connections comprises a plurality of color-coded hoses extending from the apparatus to the associated plurality of mechanical devices.

3. The apparatus of claim 1, wherein the control system comprises a programmable logic controller for automatically implementing the predetermined sequence in accordance with an operational simulation algorithm.

4. The apparatus of claim 1, wherein the control system comprises a plurality of manual controls, each for selectively actuating an associated one of the plurality of valves in accordance with a manually-operated sequence.

5. The apparatus of claim 1, wherein the control system implements the predetermined sequence of valve actuations in accordance with predetermined rotational angles associated with each of the plurality of mechanical devices.

6. The apparatus of claim 1, wherein the stamping press die can be removed from a stamping press thereby not requiring operation of the stamping press while the stamping press die undergoes testing.

7. A method for testing operation of a stamping die while said die is removed from a stamping press, comprising the steps of:
   transporting a portable testing apparatus to the location of the die;
   providing the die to be tested, said die including a plurality of mechanical devices;
   supplying input air through a plurality of pneumatic connections to an associated one of the plurality of mechanical devices;
   selecting a predetermined pressure and flow of the input air to each of the plurality of connections so as to actuate the associated mechanical devices; and
   selectively providing input air to each of the plurality of pneumatic connections, so as to implement a predetermined actuation sequence, so as to simulate a predetermined sequence of mechanical device operation.

8. The method of claim 7, wherein the step of selectively actuating comprises automatically implementing the predetermined actuation sequence in accordance with an operational simulation algorithm.

9. The method of claim 7, wherein the step of selectively actuating comprises selectively actuating the predetermined actuation sequence in accordance with a manually-operated sequence.

* * * * *